(12) United States Patent
Pevoto

(10) Patent No.: US 6,702,759 B2
(45) Date of Patent: Mar. 9, 2004

(54) INTRA-VAGINAL SELF-ADMINISTERED CELL COLLECTING DEVICE AND METHOD

(75) Inventor: Patrick S. Pevoto, Austin, TX (US)

(73) Assignee: Private Concepts, Inc., Austin, TX (US)

( * ) Notice: Subject to any disclaimer, the term of this patent is extended or adjusted under 35 U.S.C. 154(b) by 0 days.

(21) Appl. No.: 09/919,419

(22) Filed: Jul. 31, 2001

(65) Prior Publication Data

US 2003/0028123 A1 Feb. 6, 2003

(51) Int. Cl.$^7$ .............................................. A61B 10/00
(52) U.S. Cl. ........................ 600/562; 600/570; 604/1; 604/330
(58) Field of Search .................... 600/569–572; 604/1, 2, 11, 15, 18, 317, 328, 330, 358, 904, 385.17, 385.18

(56) References Cited

U.S. PATENT DOCUMENTS

| | | | |
|---|---|---|---|
| 1,932,383 A | * 10/1933 | Richardson | 604/375 |
| 2,847,000 A | 8/1958 | Nieburgs | |
| 3,726,277 A | * 4/1973 | Hirschman | 604/359 |
| 3,776,219 A | 12/1973 | Brown | |
| 3,842,166 A | * 10/1974 | Bucalo | 600/562 |
| 3,850,160 A | * 11/1974 | Denson | 600/572 |
| 3,857,384 A | 12/1974 | Watson | |
| 3,995,618 A | 12/1976 | Kingsley et al. | |
| 4,164,212 A | 8/1979 | Schuster | |
| 4,650,459 A | * 3/1987 | Sheldon | 604/15 |
| 4,735,214 A | * 4/1988 | Berman | 600/572 |
| 4,788,985 A | * 12/1988 | Manning et al. | 600/572 |
| 4,945,921 A | 8/1990 | Okimoto | |
| 4,952,204 A | 8/1990 | Korteweg | |
| 5,121,752 A | 6/1992 | Canna | |
| 5,339,828 A | 8/1994 | Keating et al. | |
| 5,445,164 A | 8/1995 | Worthen et al. | |
| 5,477,863 A | * 12/1995 | Grant | 600/572 |
| 5,725,481 A | * 3/1998 | Buck et al. | 600/572 |
| 5,830,154 A | 11/1998 | Goldstein et al. | |
| 6,143,512 A | 11/2000 | Markovic et al. | |
| 6,155,990 A | 12/2000 | Fournier | |
| 6,206,839 B1 | 3/2001 | Zwelling-Aamot | |
| 6,465,713 B1 | * 10/2002 | Gell et al. | 604/385.18 |

* cited by examiner

Primary Examiner—Charles Marmor
(74) Attorney, Agent, or Firm—Haynes & Boone, LLP

(57) ABSTRACT

An intra-vaginal self-administered cell collecting device and method includes inserting a tampon-like telescoping tube intra-vaginally. The tube includes an expandable preformed absorbent member having a textured cover. The absorbent member also includes a retrieval member extending therefrom. The tube is manipulated to expel the absorbent member intra-vaginally. The tube is removed and the absorbent member is retained intra-vaginally for a period of time. The absorbent member is retained from expanding from its preform when exposed to vaginal fluids by means of a cover on the absorbent material. The cover also captures soughed-off cells in the vaginal fluids. The absorbent material is retrieved manually by the retrieval member.

10 Claims, 2 Drawing Sheets

INTRA-VAGINAL SELF-ADMINISTERED CELL COLLECTING DEVICE AND METHOD

BACKGROUND

The disclosures herein relate generally to a Pap test device and more particularly to a cervical specimen self-sampling device.

The Pap test (sometimes called a Pap smear) is a way to examine cells collected from the cervix and vagina. This test can show the presence of infection, inflammation, abnormal cells, or cancer.

A Pap test is an important part of a woman's routine health care because it can detect abnormalities that may lead to invasive cancer. These abnormalities can be treated before cancer develops. Most invasive cancers of the cervix are preventable if women have Pap tests and pelvic exams regularly. Also, as with many types of cancer, cancer of the cervix is more likely to be treated successfully if it is detected early.

A woman should have this test when she is not menstruating; the best time is between 10 and 20 days after the first day of the menstrual period. For about 2 days before a Pap test, she should avoid douching, or using vaginal medicines or spermicidal foams, creams, or jellies (except as directed by a physician). These may wash away or hide abnormal cells.

A Pap test is simple, quick, and painless; it can be done in a doctor's office, a clinic, or a hospital. While a woman lies on an exam table, the clinician inserts a speculum into her vagina to open it. To do the test, a sample of cells is taken from in and around the cervix with a wooden scraper or a small cervical brush or broom. The specimen (or smear) is placed on a glass slide or rinsed in liquid fixative and sent to a laboratory for examination.

A physician may simply describe Pap test results to a patient as "abnormal." Cells on the surface of the cervix sometimes appear abnormal but are not cancerous. It is important to remember that abnormal conditions do not always become cancerous, and some conditions are more of a threat than others. A woman may want to ask her doctor for specific information about her Pap test result and what the result means.

When the test was first devised by George Papanicolaou, M.D., it was considered to be a test of vaginal pool cells to possibly detect uterine cancer. Fortuitously, it better detected cervical cancer. Ideally, a Pap test should capture squamous cells, which are cells from the transformation zone of the cervix. This zone is where the squamous cells and endocervical cells (including glandular cells) border upon one another. The transformation zone is where most cervical cancers originate.

There are countless women who do not obtain Pap tests every year as is recommended. This is because the test is unpleasant, painful, and for many women, it is embarrassing and/or humiliating. There are self-tests which have been developed and marketed. A benefit of the self-test is that some women who would otherwise not obtain a Pap test for the reasons given above, will be more likely to administer the self-test. However, some shortcomings of presently available self-tests are that they utilize a technology centered around fixing cells immediately in a glass slide and are designed to avoid so-called "contamination" of vaginal cells. These tests are cumbersome and produce slides that are sometimes inadequate due to an air drying artifact.

Therefore, what is needed is a self-administered Pap test which can provide a reliable sampling of cells for analysis. The present embodiments consider that vaginal pool cells are just as valuable as those obtained by the standard pap smear procedure; abnormal cells turnover much faster and slough off faster than normal cells. By testing cells in the vaginal pool, one can determine just as accurately when an abnormality exists. It is believed that each of these cell types slough off and enter the pool of vaginal fluids, which occurs through natural body fluid movement.

SUMMARY

One embodiment, accordingly, provides an intra-vaginal self-administered cell collecting device. To this end, the device includes a tampon like telescoping tube containing an expandable preformed absorbent member. A textured cover is provided on the absorbent member for capturing sloughed-off cells residing in vaginal fluids and for substantially retaining the perform of the absorbent material from expansion after exposure to the vaginal fluids.

The principal advantages of this embodiment are that a large number of cells are captured for analysis; there is a lack of the avoidance factor of desired vaginal cells; and the self-administered cell collecting device is convenient and easy to use.

DETAILED DESCRIPTION

Figure 1:
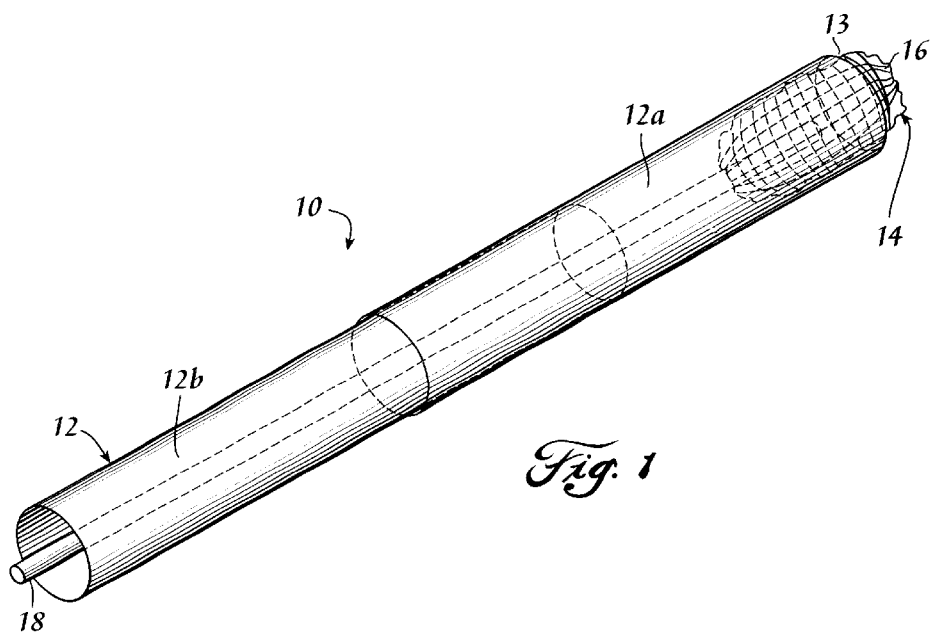
FIG. 1 is a perspective view illustrating an embodiment of a cell collecting device.

An intra-vaginal self-administered cell collecting device is generally designated 10 in FIG. 1, and includes a tampon-like telescoping tube 12 containing an expandable preformed absorbent member 14. The absorbent member 14 includes a textured cover 16, FIG. 2, for capturing sloughed-off cells residing in vaginal fluids. In addition, the textured cover 16 substantially retains the preform of the absorbent member 14 from expanding when the absorbent material 14 is exposed to the vaginal fluids. This is because without the cover 16, the absorbent material 14 will react by expanding after absorbing the vaginal fluids. This is inherent in the absorbent material, and in fact, is desired when the absorbent material is used to function as a tampon. However, in the present device, the tampon-like absorbent member 14 is restrained from expansion by the textured cover.

Figure 2:
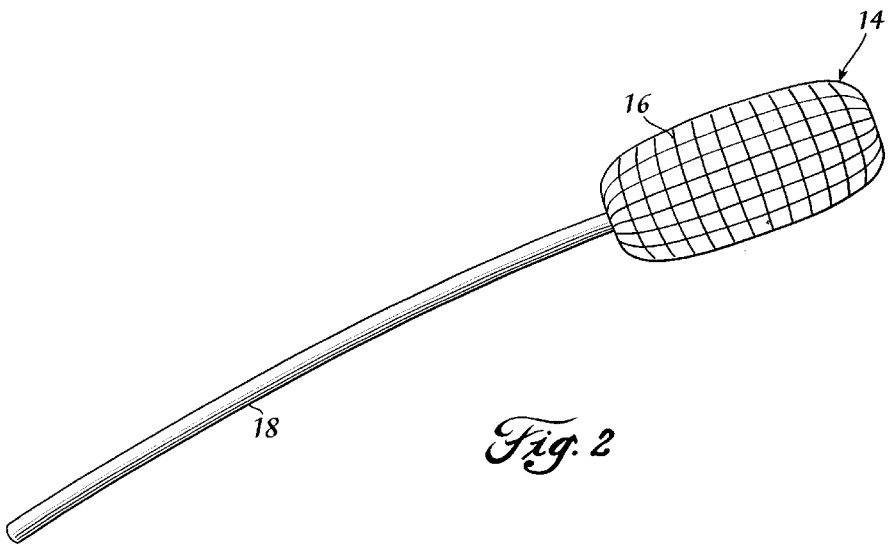
FIG. 2 is another perspective view illustrating an embodiment of an absorbent member.

The textured cover 16, FIGS. 1 and 2, is textured sufficiently to be mildly abrasive but not irritating. The purpose of the textured cover 16 is two-fold. First, the textured cover 16 is of a restrictive shape and size so as to restrain the absorbent member 14 from expanding when exposed to moisture or fluids, particularly vaginal fluids. Second, the textured cover 16 is textured to capture sloughed-off cells residing in the pool of vaginal fluids. Natural body fluid movement draws the cells into the vagina such that they desquamate into the vaginal pool including squamous cells, glandular cells and endocervical cells.

The textured cover 16 may be a separate mesh sleeve covering the absorbent member 14, or a separate member, molded and applied onto the absorbent member 14, or may be a molded outer portion of the absorbent member. As another alternative, it may be possible to add the textured cover 16 as a coating, i.e. spray applied to the absorbent member 14. In any case, the cover 16 will be porous enough to permit vaginal fluids to pass through to the absorbent member 14, will be textured enough to capture the sloughed-off cells, and will have shape stability capable of retaining the absorbent member 14 from expanding from its preform.

The telescoping tube 12 includes a first telescoping member 12a containing the preformed absorbent member 14, and a second telescoping member 12b which slides within first telescoping member 12a for expelling the preformed absorbent member 14 from an open end 13 of first member 12a. In this manner, when the tube 12 is placed intra-vaginally, movement of the second telescoping member 12b within the first telescoping member 12a, expels the preformed absorbent member 14 intra-vaginally. The tube 12 is removed after the preformed absorbent member is expelled intra-vaginally, as described above. The absorbent member 14 is retained intra-vaginally for a period of from about 30 minutes to about 4 hours. The preformed absorbent member 14 is manually retrievable by means of a flexible retrieval member 18, which is attached to and extends from the preformed absorbent member 14.

Due to the cover 16 being textured, sloughed-off cells residing in vaginal fluids are acquired and captured on the cover 16. Also, the cover 16 retains the absorbent member 14 from expanding from its preform when exposed to the vaginal fluids.

Figure 3:
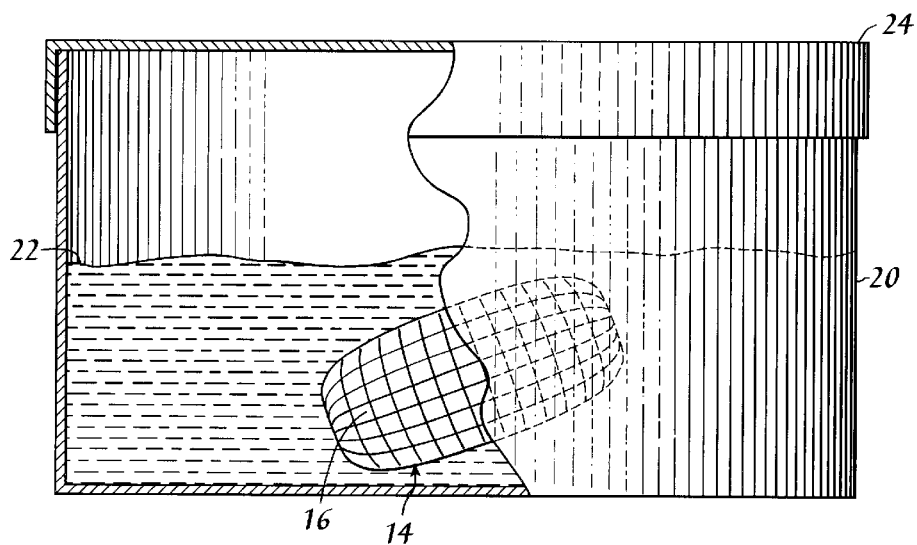
FIG. 3 is a side view illustrating an embodiment of a sealed container.
Figure 4:
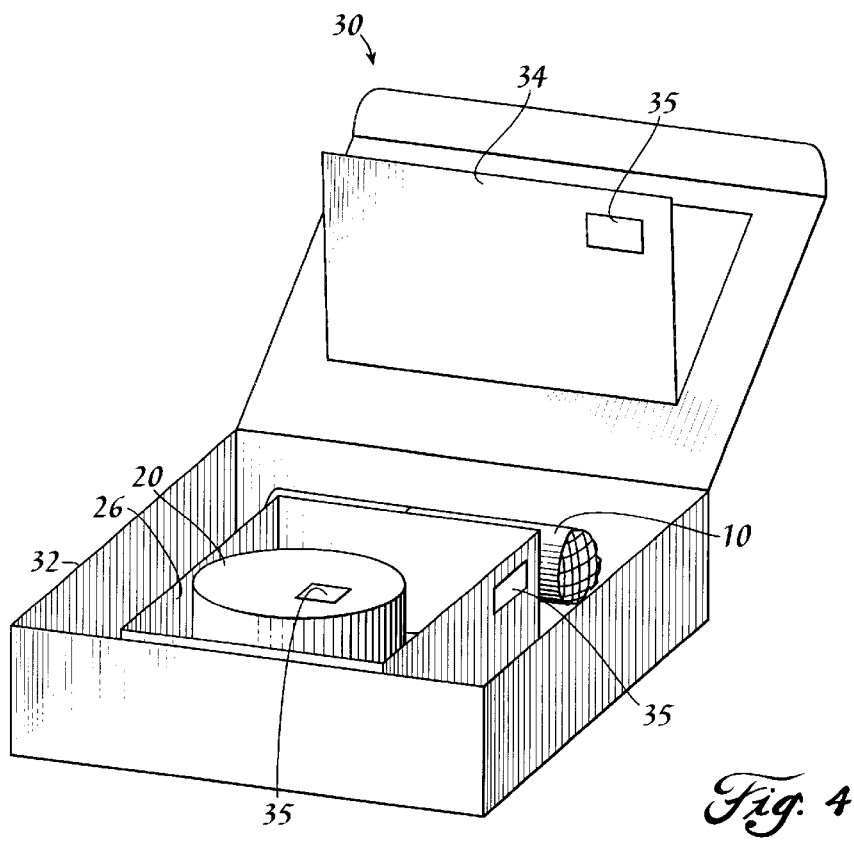
FIG. 4 is a perspective view illustrating an embodiment of a kit for self-administered cell collection.

Following retrieval of absorbent member 14, FIGS. 3 and 4, the absorbent member 14 is placed in a sealable container 20 which contains a well-known fixative 22. The container 20 is sealed by sealing cover 24. Even when in the fixative 22, the absorbent member 14 continues to be retained from expanding from its preform due to the presence of cover 16. The sealed container 20 is placed in a shipping package 26 for shipping the container 20 to a test facility which can provide the required test of the acquired cells to determine the status of the cells as is done with any other Pap test sample.

A kit 30, FIG. 4, is provided for self-administered intra-vaginal cell collection. The kit 30 is enclosed in a package 32 and includes the cell collecting device 10, the shipping package 26, the sealed container 20 and a form 34 to be completed by the user and returned with the sealed container. The form 34 is returned to the consumer with the laboratory test results. The form 34, the sealed container 20 and the shipping package 26 may include a bar code 35 to assist in maintaining user identification.

As can be seen, the principal advantages of these embodiments are that they provide an absorbent tampon device with a textured surface to encourage the sloughing of cells and absorption of these cells by the tampon. Surface texture on the absorbent tampon may be enhanced by surrounding the tampon with a polymer mesh or by compression molding of the absorbent material into a textured surface. The elongated applicator contains the tampon to facilitate placing the tampon adjacent to the cervix. The applicator has a length of approximately 15 cm and is approximately 1.4 cm in diameter.

The sealable container includes an opening larger than the tampon's maximum diameter when fully expanded and preferably twice as large as the fully expanded tampon to facilitate easy insertion of the tampon into the container by the consumer after the tampon is removed from the vaginal cavity. This container may be supplied with fixative fluid already in it so as to avoid the cost of a second solution container. Alternatively, the fixative may be delivered in a separate container that would ensure the fluid would not leak without having to seal the return container so tightly that it would be difficult for the end user to open.

The package is provided for delivery of the above-mentioned items to the consumer and for subsequent return of the tampon to a laboratory for analysis. The preferred embodiment includes a preprinted label on a non-descript box that could be delivered to the shipper without any embarrassment on the part of the consumer. The return information might be pre-printed on the outside of the package lid to minimize production costs. The package could be surrounded by a shrink-wrap cover that would prevent tampering and allow a colorful consumer focused appearance for the package that would attract attention to the product while on display for sale at a retail outlet. Instructions for use and appropriate warnings would be contained in the package or could be printed on the inside of the package lid for the consumer's convenience and reduced cost.

Also included is the form that is filled out by the consumer and returned with the sample with information required to inform the consumer of the results of the laboratory test. The form includes the bar code that matches the bar code on the sealable container to minimize the chance of mixing up samples. The form might also provide a unique password that would allow the consumer to access the test results at an Internet location without divulging any personal information.

Although illustrative embodiments have been shown and described, a wide range of modification, change and substitution is contemplated in the foregoing disclosure and in some instances, some features of the embodiment may be employed without a corresponding use of other features. Accordingly, it is appropriate that the appended claims be construed broadly and in a manner consistent with the scope of the embodiments disclosed herein.

What is claimed is:

1. A self-administered method of collecting cells temporarily residing intra-vaginally comprising:

inserting a tampon-like telescoping tube intra-vaginally, the tube including an expandable preformed absorbent member having a textured cover, the absorbent member having a retrieval member extending therefrom;

manipulating the tube for expelling the absorbent member intra-vaginally;

removing the tube;

retaining the absorbent member intra-vaginally for a period of time;

retaining the absorbent member from expanding from its preform after exposure to vaginal fluids by means of the cover on the absorbent member;

capturing sloughed-off cells residing in the vaginal fluids by means of the cover; and removing the absorbent member via the retrieval member.

2. The method as defined in claim 1 further comprising:

providing a sealable container including a fixative;

immersing the absorbent member in the fixative;

sealing the container; and retaining the absorbent member from expanding from its preform after exposure to the fixative by means of the cover on the absorbent member.

3. The method as defined in claim 2 further comprising:

providing a shipping package;

placing the container in the shipping package; and shipping the container to a test facility.

4. A self-administered method of collecting cells temporarily residing intra-vaginally comprising:

providing a telescoping tube including a flexible preformed absorbent member and a flexible retrieval member extending therefrom, the absorbent member being covered with a sleeve of a restrictive shape for substantially exposing a substantial outer surface portion of the absorbent material to vaginal contact and retaining the absorbent member from expanding from its preform after exposure to vaginal fluids, the sleeve being mildly abrasive for capturing sloughed-off cells residing in the vaginal fluids;

inserting the tube intra-vaginally;

manipulating the tube for expelling the absorbent member intra-vaginally;

removing the tube;

retaining the absorbent member intra-vaginally for a period of time; and removing the absorbent member via the retrieval member.

5. The method as defined in claim 4 further comprising:

providing a sealable container including a fixative;

immersing the absorbent material in the fixative;

sealing the container; and retaining the absorbent material from expanding from its preform after exposure to the fixative by means of the sleeve covering the absorbent material.

6. The method as defined in claim 5 further comprising:

providing a shipping package;

placing the container in the shipping package; and shipping the container to a test facility.

7. The method as defined in claim 4 further comprising:

providing a sealable container;

providing a fixative;

placing the fixative in the container;

immersing the absorbent material in the fixative; and sealing the container.

8. The method as defined in claim 7 further comprising:

providing a form; and completing the form.

9. The method as defined in claim 8 further comprising:

providing a shipping package;

placing the container and the form in the shipping package; and shipping the container to a test facility.

10. The method as defined in claim 9 wherein the container and the form are correspondingly marked for identification.

* * * * *